United States Patent [19]

Paul et al.

[11] Patent Number: 5,948,709
[45] Date of Patent: Sep. 7, 1999

[54] OIL RESISTANT POLYAMIDE BASED ADHESIVE

[75] Inventors: Charles W. Paul, Madison; Gary F. Raykovitz, Flemington, both of N.J.

[73] Assignee: National Starch and Chemical Investment Holding Corporation, Wilmington, Del.

[21] Appl. No.: 09/058,904

[22] Filed: Apr. 10, 1998

[51] Int. Cl.[6] .................................. B32B 3/02; B32B 7/12
[52] U.S. Cl. ........................ 442/327; 442/348; 528/339.5; 528/270; 524/270; 524/314; 604/385.2; 604/391; 156/330.9; 264/167; 264/145; 264/519; 264/557; 428/343
[58] Field of Search ..................... 604/385.2, 391; 528/270, 339.5; 525/66; 524/314, 270; 156/330.9; 264/557, 167, 145, 519; 428/343

[56] References Cited

U.S. PATENT DOCUMENTS

| | | | |
|---|---|---|---|
| 4,419,494 | 12/1983 | Puletti et al. | 525/95 |
| 4,626,305 | 12/1986 | Suzuki et al. | 156/164 |
| 4,652,327 | 3/1987 | Hayes et al. | 156/244.22 |
| 4,698,242 | 10/1987 | Salerno | 427/208.2 |
| 4,944,993 | 7/1990 | Raykovitz et al. | 428/290 |
| 5,024,667 | 6/1991 | Malcolm et al. | 604/382 |

FOREIGN PATENT DOCUMENTS

| | | | |
|---|---|---|---|
| WO 97/39075 | 10/1997 | WIPO | C09J 123/20 |

OTHER PUBLICATIONS

Kirk–Othmer, "Encyclopedia of Chemical Technology", *Dimer Acids,* Third Edition, vol. 7, Copper Alloys to Distallation, John Wiley & Sons, pp. 768–782.

"Thermo–Plastic Polyamide Adhesive Resins", Union Camp, Technical Bulletin.

*Primary Examiner*—Marion McCamish
*Assistant Examiner*—Arti R. Singh
*Attorney, Agent, or Firm*—Lydia T. McNally

[57] ABSTRACT

Oil resistant adhesive compositions and nonwoven articles comprising an adhesive prepared from polymeric dimer fatty acid polyamide resins which are especially suited for use in the elastic attachment of disposable nonwoven products and particularly for leg or waist bond closures for disposable products such as diapers are disclosed.

12 Claims, No Drawings

OIL RESISTANT POLYAMIDE BASED ADHESIVE

FIELD OF THE INVENTION

The present invention relates to oil resistant adhesive compositions, and to nonwoven articles comprising an adhesive prepared from polymeric dimer fatty acid polyamide resins which are especially suited for use in the elastic attachment of disposable nonwoven products and particularly for leg or waist bond closures for disposable products such as diapers.

BACKGROUND OF THE INVENTION

Elasticized leg and waist bands have gained increasing popularity in the areas of disposable applications, such as disposable diapers, feminine care products, adult incontinent products and hospital gowns.

A wide range of adhesive compositions are known and used in the construction of disposable articles. For example, it is well known that polyolefin based adhesives are suitable for the construction of diapers, particularly in the bonding of polyethylene films, or the like, to tissue or nonwoven substrates in the production of such articles. However, polyolefin based adhesives are not suitable for bonding of the elastic bands in these products because creep resistance is insufficient for such an application.

Accordingly, adhesives based on styrene such as styrene-isoprene-styrene (SIS) block copolymers or styrene-butadiene-styrene (SBS) block copolymers are used. Such flexible rubber based adhesives are the primary adhesive used for the bonding of elastic bands in the market today. However, these block copolymer adhesives lose most of their bond strength, resulting in adhesive bond failure, upon exposure to mineral oil or other oil based ointments which are often used on infants to treat skin rashes. As a result, the elastic leg bands may actually come loose from the diaper resulting in a break down of the inner leg cuff.

Polybutylene based hot melt adhesives, also a flexible adhesive product, have also been disclosed as useful for use in the attachment of elastic bands in nonwoven disposable products because of their flexibility and there resistance to oil. WO 97/39075.

It has suprisingly been found, in accordance with the present invention, that an adhesive prepared from a polymeric dimer fatty acid polyamide resin, in amounts of 70–100% of the adhesive composition, will provide bond strength for the attachment of elastic bands to disposable articles, while being resistant to exposure to mineral oil and oil based ointments. Polymeric fatty acid polyamides have been added to conventional rubbery block copolymers of the general formula A-B-A, such as SIS or SBS, in amounts of 1–20% to improve the heat and plasticizer resistance of the adhesive formulation. U.S. Pat. No. 4,419,494.

Accordingly, the adhesives disclosed herein find particular use to attach elastic bands in disposable items, particularly for leg or waist band closures on disposable diapers, adult incontinent products and other nonwoven articles.

SUMMARY OF THE INVENTION

The present invention is directed to adhesive compositions which possess certain physical properties such that it is ideally suited for use with nonwoven disposable articles. Specifically, the adhesive compositions of the present invention maintain their bond strength upon exposure to mineral oil and other oil based laminates.

Accordingly, the present invention is directed to non-woven articles comprising an adhesive composition which functions to bond elastic bands for disposable items, particularly for leg or waist band closures on disposable diapers and adult incontinent products and other nonwoven articles. Further, the present invention discloses an adhesive prepared from a dimer-fatty acid polyamide which has exceptional strength and peel adhesion even upon exposure to oil and other oil based laminates.

DETAILED DESCRIPTION OF THE INVENTION

The present invention is directed to an oil resistant adhesive composition, and to nonwoven articles comprising an adhesive prepared from polymeric dimer fatty acid polyamide resins which are especially suited for use in the elastic attachment of disposable nonwoven products such as diapers.

The primary component of the adhesive compositions used in the present invention are the polymeric dimer fatty acid polyamide resins. These resins are generally prepared by reaction, under conventional amidification conditions, of a polymeric fatty acid or mixtures thereof with other dicarboxylic acids (such as azeleic acid or adipic acid) with a diamine (such as ethylenediamine or piperazine) or mixtures thereof. Preferred polyamides are those prepared from multiacids and multiamines in which at least 40 mole percent of the multiacid is derived from unsaturated fatty acids, typically $C_{18}$ acids such as oleic, linoleic and linolenic acid. Because of their ready availability and relative ease of polymerization, oleic and linoleic acids are the preferred starting materials for the preparation of the polymeric fatty acid resins used herein. Mixtures of these two acids are found in tall oil fatty acids and, accordingly, commercial tall oil fatty acids are a common source for preparing the described polymeric fatty acid resins. Representative of polymeric fatty acids are those commercially available from the polymerization of tall oil fatty acids. The polymeric fatty acids used herein, sometimes referred to in the art as "dimer acids", are complex mixtures resulting from the polymerization of fatty acids. These polymeric fatty acids have a typical composition as follows:

PERCENT BY WEIGHT $C_{18}$ monobasic acids (monomer) 0–5
$C_{36}$ dibasic acids (dimer) 60–95
$C_{54}$ and higher polybasic acids (trimer) 1–35

These multiacids used in the preparation of the dimer fatty acid polyamide resins are prepared by self condensation of unsaturated fatty acids to produce "dimer" acids. However, the dimerization process typically produces up to about 25% of triacid as well. The relative ratios of monomer, dimer, and trimer in unfractionated polymeric fatty acids are dependent on the nature of the starting material and the conditions of polymerization. For purposes of this invention the term dimer acid is meant to include small amounts of trimer acid. The preparation of these dimer acids is further described in *Encyclopedia of Chemical Technology*, "Dimer Acids", E. Leonard, 3 ed., vol. 7, p. 768, Wiley (1979). Methods for the polymerization of fatty acids are described, for example, in U.S. Pat. No. 3,157,681. The polymeric fatty acids may be unhydrogenated or hydrogenated.

A wide variety of dicarboxylic acids may be employed in the preparation of the polyamides described above, including aliphatic, cycloaliphatic and aromatic dicarboxylic acids. Representative of such acids, which may contain from 2 to 22 carbon atoms, are oxalic, glutaric, malonic, adipic, succinic, suberic, sebacic, azelaic, pimelic, terephthalic, isophthalic, phthalic, naphthalene dicarboxylic acids and 1,4- or 1,3-cyclohexane dicarboxylic acids. Methods of preparing these preferred acids are well known, and they are readily available commercially.

Preferred dicarboxylic acids are the straight chain aliphatic diacids having at least 6 carbon atoms and more preferably 6 to 22 carbon atoms such as azelaic, sebacic, 1,18-octadecane dicarboxylic and 1,16-hexadecane dicarboxylic acids. It should be understood that use of the corresponding acid anhydrides, esters, and acid chlorides of these acids is included in the term "dicarboxylic acid".

The organic diamines used to prepare the dimer fatty acid polyamide resins of the present invention may be one or more of the known aliphatic, cycloaliphatic or aromatic diamines having from about 2 to 20 carbon atoms. Preferred especially are the alkylene diamines. Illustrative of the preferred diamines are ethylene diamine, 1,3-diaminopropane, 1,4-diaminobutane, terephthalyl diamine, known as p-xylene diamine, 1,6-hexamethylene diamine, 4,4'-methylenebis(cyclohexylamine), 2,2-bis-(4-cyclohexylamine) propane, polyglycol diamines, isophorone diamine, isophthalyl diamine, known as m-xylene diamine, cyclohexanebis(methylamines), 1,4-bis-(2'-aminoethyl)benzene and 4,4'-methylenebis (cyclohexylamine). These diamine compounds are all prepared by well known methods and many are commercially available. Preferred particularly are the straight chain aliphatic diamines of 2 to 20 carbons atoms, especially ethylene diamine and hexamethylene diamine, and cycloaliphatic diamines, especially 4,4'-methylenebis(cyclohexylamine).

The stoichiometry of the polymerization of the multiacids and multiamines is controlled to yield the desired molecular weight and either predominately amine or predominately acid end groups. Polyamides of this type are described in the above-noted reference and also in the *Handbook of Adhesives* "Polyester and Polyamide High Performance Hot Melt Adhesives", C. Rossifto, 3 ed., p. 478, I. Skeist editor, Van Nostrand-Reinhold (1990). Typical of the dimer fatty acid polyamides of this type are the Uni-Rez® polyamides sold by Union Camp Corporation. Suitable other polymeric fatty acid polyamides may be obtained from General Mills (Henkel) under the tradenames "Versamid", and "Macromelt".

The most preferred dimer fatty acid polyamide resins will have a softening point greater than 115° C., most preferably greater than 125° C. An example of a preferred dimer fatty acid polyamide resin for use in the present invention is UNI-REZ® 2638 available from Union Camp, N.J., which has a softening point of 142° C.

The dimer fatty acid polyamides resins may be used alone or in combination with known adhesive ingredients. If the dimer fatty acid polyamide resins are present in an adhesive composition 70 to 100% by weight based on the weight of the composition will be used. Preferably adhesive compositions of the present invention comprise the dimer fatty acid polyamide resins alone as the only adhesive component.

The adhesive compositions of the present invention may also comprise tackifying resins which serve to extend the adhesive properties of the polyamide resin. Tackifying resins suitable for use herein include: (1) polyterpene resins having a softening point, as determined by ASTM method E28 58T, of from about 60° to 140° C., which are the product of the polymerization of terpene hydrocarbons, such as the bicyclic mono-terpene known as pinene in the presence of Friedel-Crafts catalysts at moderately low temperatures; (2) phenolic-modified terpene resins such, for example, as the resin product resulting from the condensation in an acidic medium, of a bicyclic terpene and a phenol; (3) aliphatic petroleum hydrocarbon resins having a Ball and Ring softening point of from about 60° to 140° C., which generally are the polymerization product of monomers consisting primarily of olefins and diolefins; (4) hydrogenated copolymers of alpha-methyl styrene and styrene having a softening point of about 78° C. to 125° C.; and (5) rosin and esters of rosin formed by condensation with polyols such as glycerol or pentaerythritol. Other tackifying resins suitable for use herein will be familiar to one of skill in the art.

Especially preferred tackifying resins are the phenolic modified terpenes.

These tackifying resins are present in an amount of 10% to 45%, preferably 20 to 40% by weight of the adhesive.

The adhesive compositions of the present invention may also comprise a stablilizer or antioxidant. Antioxidants for use herein include high molecular weight hindered phenols and multifunctional phenols such as sulfur and phosphorous-containing phenols. Hindered phenols are well known to those skilled in the art and may be characterized as phenolic compounds which also contain bulky radicals in close proximity to the phenolic hydroxyl group thereof. In particular, tertiary butyl groups generally are substituted onto the benzene ring in at least one of the ortho positions relative to the phenolic hydroxy group. The presence of these radicals in the vicinity of the hydroxyl group serves to retard its stretching frequency and correspondingly, its reactivity. This steric hindrance thus provides the phenolic compound with its stabilizing properties.

Representative hindered phenols include: 1,3,5-trimethyl-2,4,6-tris(3,5-di-tert-butyl-4-hydroxybenzylbenziene; pentaerythrityl tetrakis-3(3,5-di-tert-butyl-4-hydroxy-phenyl)-propionate,n-octadecyl-3(3,5-di-tert-butyl-4-hydroxyphenyl)propionate, 4,4'-methylenebis(2,6-di-tert-butylphenol); 2,2'-methylenebis (4-methyl-6-tert-butylphenol); 4,4'-thiobis(6-tert-butyl-o-cresol); 2,6-di-tert-butylphenol; 6-(4-hydroxyphenoxy)-2,4-bis-(n-octylthio)-1,3,5 triazine; 2,4,6-tris(4-hydroxy-3,5-di-tert-butylphenoxy)-1,3,5-triazine; di-n-octadecyl-3,5-di-tert-butyl-4-hydroxy-benzylphosphonate; 2-(n-octylthio)-ethyl) 3,5-di-tert-butyl-4-hyroxy-benzoate, and sorbitol hexa-[3-(5-di-tert-butyl-4-hydroxy-phenyl)propionate.] Preferred antioxidant for use herein includes IRGANOX 1098 available from Ciba Geigy.

The antioxidant is generally present at levels of 0.2 to 2% by weight based upon the total weight of the composition.

The performance of these antioxidants may be further enhanced by utilizing, in conjunction therewith synergists such, for example, as thiodipropionate esters and phosphites; and chelating agents and metal deactivators such, for example, as ethylenediamine tetraacetic acid.

Optional additives may be incorporated in minor amounts, generally less than 3% by weight, into the compositions in order to modify certain properties thereof. Among these additives may be included colorants such as tianum dioxide; fillers such as talc and clay, etc., hydrocarbon process oils; and other additives familiar to one of skill in the art.

Preferred compatible plasticizers include phthalate plasticizers such as dioctyl phthalate; butyl benzyl phthalate (e.g., SANTIZER 160 available from Monsanto); liquid polyesters such as DYNACOL 720 from Hüls; benzoate plasticizers such as diethylene glycol dibenzoate (e.g., BENZOFLEX 50 from Velsicol) and diethylene glycol benzoate where the mole fraction of hydroxyl groups which have been esterified ranges from 0.5 to 0.95; citric acid esters such as triethyl citrate (e.g., CITROFLEX 2 from Morflex); phosphate plasticizers such as t-butylphenyl diphenyl phosphate; poly(ethylene glycols) and derivatives thereof such as the phenyl ether of poly(ethylene glycol) (e.g., PYCAL 94 available from ICI) as well as liquid rosin derivatives having Ring and Ball melting points below about 60° C. such as the methyl ester of hydrogenated rosin (e.g., HERCOLYN D from Hercules); as well as vegetable and animal oils such as glyceryl esters of fatty acids and polymerization products thereof. Preferred plasticizers include SANTICIZER 160, BENZOFLEX 50 and CITROFLEX 2, with BENZOFLEX 50 most preferred. The plasticizers are present in amount of 0–15% based on the total weight of the composition.

Other applications conventionally employing adhesives based on these polyamide polymers may require the use of wax diluents in order to reduce the melt viscosity or cohesive characteristics of the adhesive compositions without appreciably decreasing their adhesive bonding characteristics. These waxes are often used in adhesives which do not exhibit pressure sensitive properties.

Suitable waxes include N-(2-hydroxyethyl)-12-hydroxy stearamide wax, hydrogenated castor oil, oxidized synthetic waxes, N,N'-ethylenebisstearamide, poly(ethylene oxide) having a weight average molecular weight above about 1000 and functionalized synthetic waxes such as carbonyl containing ESCOMER H101 from Exxon.

The wax component will be present in amount of 0 to 15% based upon the total weight of the adhesive composition.

These adhesives may be formulated using techniques known in the art. An exemplary procedure involves adding the dimer fatty acid polyamide resins to a high shear mixer such as a sigma blade mixer at elevated temperatures, allowing it to form a smooth melt, followed by the addition of any other ingredients.

The resultant adhesives may be used in the assembly or construction of various disposable applications including, but not limited to, disposable diapers, adult incontinent products, feminine care products, hospital gowns, bed pads and the like.

The adhesive composition of this invention is especially useful for elastic attachment in disposable nonwoven products, such as diapers, to bond various elastic materials to porous and nonporous substrates such as nonwoven, tissue, polyethylene, polypropylene, and the like. Even when exposed to oil, the adhesive composition provides good elastic attachment bonds when tested via standard creep resistance and peel strength test methods.

Accordingly, the adhesive compositions of the present invention possess, depending upon the particular formulation, sufficient creep resistance to perform as an elastic attachment adhesive in a nonwoven disposable article, sufficient bond strength to perform as a construction adhesive in a nonwoven disposable article, maintenance of acceptable bond strength after oil exposure, and good peel adhesion to polyolefin after elevated temperature aging.

The present invention also contemplates the use of the adhesive compositions in nonwoven products for bonding porous and nonporous substrates such as nonwoven, tissue, polyethylene, polypropylene, and the like to one another.

The following examples are illustrative of the present invention and are not intended to limit the scope and claims of the present invention in any way.

In the following illustrative examples all parts are given by weight and all temperatures in degrees Celsius unless otherwise noted.

EXAMPLE I

Three polyamide resins were tested. These resins are UNI-REZ® 2638, UNI-REZ® 2643 and UNI-REZ® 2692, dimer fatty acid polyamide resins available from Union Camp. These resins are designated Adhesives I, II and III respectively in Table I. The resins were applied by swirl spray at 9.4 g/m$^2$ on a J and M lab coater to 2 Lycra elastic strands stretched 250%. The sprayed strands were bonded between two non-woven sheets of polyolefin having an areal density of 0.6oz/yd$^2$. The bonded sandwich was conditioned overnight at 73° F./50% RH and then tested for creep resistance. The bonded sandwich was exposed to oil, as described below, and the creep resistance was measured again. The oil used of KAYDOL oil, a U.S.P. grade white oil from Witco Corporation.

The creep test consisted of stretching about 25 cm of material to its full elongation, stapling it in place to a cardboard sheet, marking a 20 cm length on the elastics, cutting the elastics 1 cm outside of this 20 cm portion on each side, and placing the sample in an oven at 40° C. The retraction of the elastics, as measured between the marks, is monitored and reported as percent creep=Δ length/20 cm. In examples where the bond was exposed to oil, the oil was soaked through the bonded sandwich prior to cutting the elastics.

The test was repeated with a control, which is a conventional rubber based adhesive formulation.

The results are reported in Table 1. All three polyamides exhibit good creep resistance, when compared to the control. Even when exposed to oil, all three polyamides exhibit good creep resistance compared to the control. The rubber-based formulation relaxes fully in one hour whereas none of the polyamides exhibit full creep even after four hours. (A value of 71% indicates full relaxation of elastic at 250% elongation.) Unirez 2638 is clearly the best product, exhibiting <10% creep with or without oil.

TABLE I

| Adhesive | | Open Time (Sec) | Soft Pt. R&B (° C.) | Viscosity (cP) 325° F. | Viscosity (cP) 350° F. | Spray T (° F.) | Creep (%) after 4 hours No oil | Creep (%) after 4 hours With Oil |
|---|---|---|---|---|---|---|---|---|
| I | lot A | 20 | 142 | 10,200 | — | 350 | 3.6 | 4.5 |
|   | lot B |    |     | 7,700  | 4,813 | 325 | 7.5 | 7.5 |
| II |      | 10 | 125 | 5,975  | 3,525 | 325 | 10.5 | 39 |
| III |     | 450 | 115 | 5,560 | —     | 325 | 30.3 | 66 |
| Control | | — | — | —      | 15,000 | 375 | 3.0 | 71 |

EXAMPLE II

The maximum peel force of nonwoven laminates similar to that described in Example I was determined. In this test a dimer fatty acid polyamide resin available from Union Camp under the designation X35-792-26, Adhesive IV, with softening point of 133° C. was used and compared to a conventional rubber-based adhesive and a conventional olefin-based construction adhesive. Samples were one inch wide with an adhesive level of 20g/m$^2$. Peel was transverse to the machine direction at 10 in/min. Measurements were taken. Another set of samples were soaked overnight in KAYDOL oil, from Witco Corporation, and the measurements repeated. The results are shown below in Table II:

TABLE II

| | Peel Strength (grams) | | |
|---|---|---|---|
| | Dry | Oil | % Retention |
| Conventional Rubber-Based Adhesive | 1210 ± 123 | 51 ± 10 | 4 |
| Conventional Olefin-Based Construction Adhesive | 873 ± 72 | 57 ± 67 | 6 |
| Adhesive IV | 624 ± 57 | 354 ± 29 | 57 |

The polyamide showed significant retention even after soaking overnight in oil, as compared to the conventional adhesives.

EXAMPLE III

A Rheometrics Dynamic Mechanical Analyzer (Model RDA 700) was used to obtain the elastic (G') and loss (G") moduli versus temperature. The instrument was controlled by Rhios software version 4.3.2. Parallel plates 8 mm in diameter and separated by a gap of about 2 mm were used. The sample was loaded and then cooled to about −100° C. and the time program started. The program test increased the temperature at 5° C. intervals followed by a soak time at each temperature of 10 seconds. The convection oven containing the sample was flushed continuously with nitrogen. The frequency was maintained at 10 rad/s. The initial strain at the start of the test was 0.05% (at the outer edge of the plates). An autostrain option in the software was used to maintain an accurately measurable torque throughout the test. The option was configured such that the maximum applied strain allowed by the software was 80%. The autostrain program adjusted the strain at each temperature increment if warranted using the following procedure. If the torque was below 200 g-cm the strain was increased by 25% of the current value. If the torque was above 1200 g-cm it was decreased by 25% of the current value. At torques between 200 and 1200 g-cm no change in strain was made at that temperature increment. The shear storage or elastic modulus (G') and the shear loss modulus (G") are calculated by the software from the torque and strain data. Their ratio, G"/G', also known as the tan delta, was also calculated.

Adhesives I, II and IV, from Examples I and II, were measured and compared to a control which is a conventional rubber based elastic attachment adhesive available from National Starch and Chemical Company. The results are shown in Table III:

TABLE III

| Adhesive | G' ($10^6$ dynes/cm$^2$) at 25° C. |
|---|---|
| I | 23 |
| II | 140 |
| IV | 30 |
| Control | 2.6 |

The results show that the polyamide resins are not as flexible as the conventional rubber based adhesive usually used in the attachment of elastic bands in disposable articles.

We claim:

1. A nonwoven product comprising an elastic attached to at least one nonwoven substrate with an adhesive comprising 70–100% by weight of a dimer fatty acid polyamide resin having a softening point greater than 115° C.

2. A nonwoven product according to claim 1 wherein the non woven articles comprise diapers, feminine products, hospital gowns and adult incontinent products.

3. A method for preparing non woven articles comprising applying the adhesive of claim 2 to elastic bands for leg or waist band closures.

4. An oil resistant adhesive composition for attaching elastic bands in non woven products comprising 70–100% by weight of a dimer fatty acid polyamide resin having a softening point greater than 115° C.

5. The method of claim 3 wherein the non woven articles are selected from the group consisting of disposable diapers, feminine products, hospital gowns and adult incontinent products.

6. An oil resistant adhesive according to claim 4 wherein the non woven products comprise diapers, feminine products, hospital gowns and adult incontinent products.

7. A bonding agent for elastic bands for non woven products comprising the adhesive of claim 4.

8. A bonding agent for elastic bands for leg or waist band closures on disposable diapers, feminine products, hospital gowns and adult incontinent products comprising the adhesive of claim 4.

9. An article comprising an elastic band attached to the article with the adhesive of claim 4.

10. The article of claim 9 wherein the article is selected from the group consisting of disposable diapers, feminine products, hospital gowns and adult incontinent products.

11. A nonwoven product comprising an elastic attached to at least one nonwoven substrate with an adhesive comprising 100% by weight of a dimer fatty acid polyamide resin having a softening point greater than 115° C.

12. An oil resistant adhesive composition for attaching elastic bands in non woven products comprising 100% by weight of a dimer fatty acid polyamide resin having a softening point greater than 115° C.

* * * * *